United States Patent [19]
Ralph et al.

[11] Patent Number: 4,743,540
[45] Date of Patent: May 10, 1988

[54] METHOD FOR DIAGNOSIS OF SUBCLASSIFICATIONS OF COMMON VARIED IMMUNODEFICIENCY DISEASE GROUP

[75] Inventors: Peter Ralph, Purdys, N.Y.; Osamu Saiki, Nara, Japan

[73] Assignee: Memorial Sloan-Kettering Cancer Center, New York, N.Y.

[21] Appl. No.: 536,283

[22] Filed: Sep. 27, 1983

[51] Int. Cl.⁴ .................. C12Q 1/68; C12Q 1/04; G01N 33/53; G01N 33/566

[52] U.S. Cl. .................................. 435/6; 435/7; 435/29; 435/35; 436/501; 436/513; 436/519

[58] Field of Search ............... 436/501, 546, 548, 519, 436/513; 435/4, 35, 29, 76

[56] References Cited

U.S. PATENT DOCUMENTS 3,988,115 10/1976 Modabber ..................... 436/546
4,284,412 8/1981 Hansen et al. .................. 436/548

OTHER PUBLICATIONS

Mitsuya et al., J. Immunol., 127 (1981) 311–315.
Chapman et al., Chem. Abstracts, 88 (1978) #168277m.
Peter et al., Chem. Abstracts, 100 (1984) #33156s.
Denis et al., J. Immunol., 131 (1983) 2273–8.
Schuurman et al., J. Immunol., 125 (1980) 820–6.
Saiki et al., J. Immunol., 127 (1981) 1044–7.
Gearhart, Nature, 269 (1977) 812–13.
Mongini et al., J. Exp. Med., 155 (1982) 884–902.
Saiki et al., Clin. Immunol. Immuno Pathol., 25, 114–25 (1982).
Saiki et al., Proc. Nat'l Acad. Sci. USA, 79, 6008–12 (Oct., 1982).
Peter et al., International Lymphokine Workshop (3rd 1982) Haverford College, pp. 677–685.

*Primary Examiner*—Christine M. Nucker
*Attorney, Agent, or Firm*—John P. White

[57] ABSTRACT

A method is devised to assay and diagnose common varied immunodeficiency syndrome. This syndrome is subdivided or subset into at least four separate groups of B-cell deficiencies based on a patients peripheral blood B-cell proliferative and/or differentiative response to various stimulatory factors alone or in combination. CVI diagnosis and therapy are aided by this invention.

4 Claims, No Drawings

METHOD FOR DIAGNOSIS OF SUBCLASSIFICATIONS OF COMMON VARIED IMMUNODEFICIENCY DISEASE GROUP

The present invention was partially made with grants CA-19267, CA-08748, AI-19495, NS-11851 and AG-03592 from the U.S. National Institutes of Health. Therefore, the U.S. Government has certain rights in this invention.

The present invention relates to a method for subclassification of common varied immunodeficiency using stages of B-cell defects.

BACKGROUND

Acquired or common varied immunodeficiency (CVI) is a heterogeneous collection of diseases characterized by low levels of immunoglobulins (Igs) and specific antibodies, especially IgG and IgA, but having percentages of B lymphocytes in blood ranging from low to greater than normal. Deficiencies in the capacity of CVI cells to secrete Ig, assayed in vitro [Wu, L., et al. (1973) J. Clin. Invest. 52, 3180–3189; Geha, R.S., et al., (1974) N. Engl. J. Med. 291, 1–6; de La Concha, E.G., et al., (1977) Clin. Exp. Immunol. 27, 208–215; Schwartz, S., et al., (1977) J. Clin. Invest. 59, 1176–1187; Siegal, F.P., et al. (1978) N. Engl. J. Med. 299, 172–178], and the variable-to-low numbers of plasmacytes in lymphoid tissues (Siegal, F.P., et al, (1977) Clin. Heamatol. 6, 355–422) demonstrate a profound defect in B-cell maturation in this disease. One or more defects in B cells are considered to be the primary cause of the disease in many cases of CVI (Wu, L, et al. Supra, de la Concha, E.G., et al. Supra, Siegal, F.P., et al. (1978) Supra). T-cell functions are also abnormal in 50–60% of patients (de la Concha, E.G., et al. Supra; Waldmann, T.A., et al., (1978) Ann. Intern. Med. 88, 226–238; World Health Organization (1979) Clin. Immunol. Immunopathol. 13, 296–359). High levels of suppressor T cells (de la Concha, E.G. et al., Supra; Siegal, F.P., (1978) Supra; Cunningham-Rundles, S., et al. (1981) J. Clin. Immunol. 1, 65–72) or suppressor monocytes (Siegal, F.P., et al. (1978) Supra) have been found in an occasional CVI patient, shown by inhibition of immune responses of normal donor cells in cocultures. However, replacement of suppressor T-cell populations with normal allogeneic T cells usually does not prevent the deficiency of patient B cells in in vitro assays.

Pokeweed mitogen (PWM) stimulation has been a standard assay to assess the functional capacity of B cells in peripheral blood to secrete Ig, although it is T cell dependent in its action (Wu, L., et al., Supra; Geha, R.S., et al. Supra; de la Concha, E.G., et al. Supra; Schwartz, S., et al. Supra; Siegal, F.P., et al. (1978) Supra; Siegal, F.P., et al. (1977) Supra; Cunningham-Rundles, S., et al. Supra). We have described improved conditions for induction of B-cell differentiation using PWM and B-cell mitogen Staphylococcus aureus strain Cowan I (herein called Cowan I) (Saiki, 0., et al, (1981) J. Immunol. 127, 1044–1047). High numbers of Ig-secreting cells are obtained in cultures of all normal donors tested, even if they are low responders to either mitogen alone or have excess levels of T-cell suppression (Saiki, 0, et al. (1982) Cell Immunol., in press). Cowan I is a T-cell independent mitogen for B cells (Fosgren, A., et al. (1976) Eur. J. Immunol. 6, 207–212; Schuurman, K.R.B., et al. (1980) J. Immunol. 125, 820–824), and proliferative responses to this agent have been studied in CVI. Schuurman, et al. (Schuurman, K.R.B., et al., Supra) found a correlation of Cowan I-induced DNA synthesis and the presence of B cells in the blood of 11 cases of severe combined immunodeficiency, agammaglobulinemia, or CVI. We have described goat F(ab')$_2$ fragment antibodies to IgM and IgD that also are T-cell independent mitogens for B cells (Saiki, 0., et al. (1982) Clin. Immunol. Immunopathol., in press). The purpose of the present invention is to show that differences in B-cell proliferation, and differences in Ig secretion by stimulatory means in CVI determines B-cell subsets or stages of differentiation. These subsets of CVI will then serve as diagnostic and therapeutic tools. This is an unexpected result from the use of B-cell mitogens, and such B-cell mitogens in varying combinations. Therefore, it will be obvious to those skilled in the art to use such mitogens in combinations other than those illustrated below. The invention therefore is not limited to the combinations shown, these are for illustrative purposes. Other mitogen combinations may serve as well.

SUMMARY

Various B-cell stimulatory factors are used in varying combinations to assay peripheral blood from patients with CVI. Distinct subsets of the syndrome are thereby detected differing in their proliferative and differentiation responses to these varying factors. Such subsets or classes are of use in the diagnosis and further course of therapy for these different immunodeficiency manifestations. The work of the present invention is described in a published paper Saiki, et al. PNAS. U.S.A., 79:6008 (1982) which is hereby incorporated by reference.

DESCRIPTION

Example of Cell Preparations

Peripheral blood mononuclear cells were obtained from patients or normal adult volunteers by centrifuging heparinized venous blood on Ficoll/Hypaque and washing three times in Hanks' balanced salt solution (HBSS). B and T cells were separated by one or two cycles of rosetting with neuraminidase-treated sheep erythrocytes, followed by Ficoll/Hypaque centrifugation (Saiki, 0. et al.(1981) Supra). Monocytes were partially depleted by incubation for 16 hr. on plastic tissue culture dishes in culture medium (alpha minimal essential medium, GIBCO, Grand Island, New York) containing penicillin, streptomycin. 0.2mM glutamine, and 10% fetal calf serum. Residual monocytes were assayed by latex bead phagocytosis (Ralph, P. et al. (1977) Cancer Res. 37, 546–550).

Example of T-Cell-Replacing Factor.

Mononuclear cells were isolated from a spleen of a patient with Hodgkin disease which spleen was not involved pathologically. The cells were irradiated with 1,000 R (1R=2.58×10$^4$ C/kg) to enhance factor production (Saiki, O. et al, (1982) Supra) and cultured at 2×10cells per ml in 1% fetal calf serum with 0.25% PWM (GIBCO, Grand Island, N.Y.) for 2 days. The supernatant was concentrated 20-fold by Amicon pressure filtration and fractionated on a Sephadex G-100 column as described (Hirano, T. et al. (1981) J. Immunol. 126, 517–521).

Example of Mitogenic Assays

Cells were cultured in flat-bottom microtiter plates (3040, Falcon) in triplicate, with each microwell containing $1 \times 10^5$ cells in 0.2 ml of culture medium. Mitogen prepared in HBSS, or an equivalent volume of HBSS used as control, was added to the wells, and they were incubated for 3 days at 37° C. in humidified 5% $CO_2$/95% air. Final concentrations of 0.25% PWM, 0.01% (vol/vol) Cowan I (Saiki, et al. (1981) Supra; 10% formaldehyde- and heat-killed, Calbiochem-Behring), or 10 microgram of goat F(ab')$_2$ fragment of anti-Ig mu chain per ml (Saiki, et al. (1982) Supra) were used. One microcurie of [$^3$H]thymidine (6 Ci/mmol, New England Nuclear; 1 Ci=$3.7 \times 10^{10}$ becquerels) was added for the last 4 hr. The cells were harvested and washed on glass filters, and [$^3$H]thymidine incorporation was determined by liquid scintillation.

Example of Differentiation to Ig-Secreting Cells

Cells were cultured as above for 6 days with 0.025% PWM, 0.01% Cowan I, or 0.25% PWM plus 0.001% Cowan I - optimal concentrations for each mitogen condition for the induction of Ig-secreting cells with normal donor peripheral blood mononuclear cells (Saiki, 0. et al. (1981) Supra). Cells were washed and resuspended to HBSS for assay of Ig-secreting cells by reverse hemolytic plaques with protein A-coated sheep erythrocytes and specific anti-IgM, -IgG, or -IgA antisera as described (Saiki, 0. et al. (1981) Supra). For stimulation of B cells with T-cell-replacing factor, 0.025% Cowan I was used (Saiki, 0. et al. (1981) Supra).

Examples of Mitogenic and Differentiative Defects in Patient B-Cell Responses The clinical parameters of the immunodeficient patients studied are listed in Table 1 below. Fourteen patients have CVI with low serum Ig levels and variable-to-low numbers of blood B cells. Patient 15 has X chromosome-linked agamma-globulinemia with no detectable B cells. All patients are being treated with 300 mg of gammaglobulin (Swiss Red Cross, Sandoglobulin) per kg of body weight, administered intravenously at intervals of 2-3 wk. Patients were studied on the days of and prior to these infusions. The levels of Ig expressed in Table 1 reflect pretreatment values obtained before initiation of gammaglobulin therapy.

TABLE 1

Examples of Clinical parameters of immunodeficiency patients

| Patient # | Age | Sex | Serum Ig* IgM | IgG | IgA | % B cells+ |
|---|---|---|---|---|---|---|
| 1 | 60 | F | 84 | 175 | 0 | 11.5 |
| 2 | 37 | F | 160 | 276 | 0 | 4.5 |
| 3 | 33 | M | 0 | 10 | 10 | 10 |
| 4 | 40 | F | 137 | 470 | 97 | 10.5 |
| 5 | 33 | M | 9 | 130 | 0 | 7 |
| 6 | 14 | F | 30 | 405 | 77 | 12 |
| 7 | 14 | M | 190 | 164 | 0 | 5.5 |
| 8 | 18 | F | 6 | 812 | 57 | 20 |
| 9 | 18 | F | 20 | 1,180 | 48 | 19 |
| 10 | 33 | M | 24 | 288 | 32 | 9 |
| 11 | 19 | M | 1 | 109 | 0 | 16 |
| 12 | 16 | F | 34 | 254 | 0 | 13 |
| 13 | 7 | M | 0 | 108 | 4 | 0-1 |
| 14 | 32 | F | 0 | 48 | 10 | 1.5 |
| 15 | 11 | M | 0 | 0 | 120 | 0 |

*In mg/dl; normal ranges for adults, 80-350 mg of IgM, 800-1,800 mg of IgG, and 90-450 mg of IgA per dl. 0, Undetectable.
+Percentage of blood mononuclear cells staining with polyvalent anti-Ig; normal range, 3-20%.
chromosome-linked agammaglobulinemia.

Peripheral blood mononuclear cells from the clinical examples of Table I above had high mitogenic responses to PWM (Table 2) below. The first four patients (group I) also showed good mitogenic responses to the T-cell-independent B-cell mitogens Cowan I and anti-mu and produced nearly normal numbers of mitogen-induced IgM-secreting cells. However, almost no secretion of IgG or IgA was detected in these cultures in contrast to the results with normal donors. The next group (II) of six patients also showed B mitogenic responses but generated no Ig-secreting cells in culture. The last group (III) of five patients showed no proliferation or differentiation of Ig-secreting cells. Thus, patients with this heterogeneity of clinical diseases formed clearly distinct groups based on specific B-cell assays.

TABLE 2

Examples of Mitogenic and Ig-secreting defects of patient peripheral blood mononuclear cells*

| Group | Patient # | Mitogen response, cpm 0 | Cowan I | Anti-mu | PWM | IgSC induced per 10$^4$ cells IgM | IgG | IgA |
|---|---|---|---|---|---|---|---|---|
| I | 1 | 201 ± 23 | 4,870 ± 879 | 631 ± 39 | 3,596 ± 884 | 848 ± 23 | 11 ± 2 | 19 ± 4 |
| | 2 | 177 ± 47 | 1,667 ± 291 | 1,323 ± 147 | 7,056 ± 263 | 318 ± 20 | 2 ± 1 | 0 |
| | 3 | 321 ± 25 | 1,345 ± 52 | 727 ± 101 | 10,660 ± 1,052 | 127 ± 6 | 8 ± 3 | 4 ± 1 |
| | 4 | 206 ± 19 | 2,960 ± 680 | 942 ± 59 | 3,095 ± 185 | 408 ± 23 | 0 | 0 |
| II | 5 | 194 ± 21 | 8,021 ± 174 | 3,888 ± 192 | 7,374 ± 965 | 0 | 0 | 0 |
| | 6 | 242 ± 61 | 1,982 ± 69 | 1,956 ± 318 | 9,603 ± 1,426 | 0 | 0 | 0 |
| | 7 | 205 ± 23 | 3,899 ± 497 | 1,535 ± 213 | 8,950 ± 291 | 0 | 0 | 0 |
| | 8 | 198 ± 18 | 6,022 ± 713 | 868 ± 44 | 2,101 ± 136 | 0 | 0 | 0 |
| | 9 | 208 ± 26 | 9,849 ± 770 | 488 ± 93 | 2,040 ± 323 | 0 | 0 | 0 |
| | 10 | 216 ± 9 | 7,115 ± 394 | 1,027 ± 176 | 19,479 ± 1,065 | 0 | 0 | 0 |
| III | 11 | 245 ± 34 | 256 ± 32 | 288 ± 35 | 11,841 ± 738 | 0 | 0 | 0 |
| | 12 | 244 ± 52 | 286 ± 33 | 233 ± 22 | 10,821 ± 1,473 | 0 | 0 | 0 |
| | 13 | 139 ± 27 | 135 ± 56 | 148 ± 68 | 2,142 ± 557 | 0 | 0 | 0 |
| | 14 | 123 ± 7 | 172 ± 12 | 119 ± 20 | 6,089 ± 199 | 0 | 0 | 0 |
| | 15 | 304 ± 31 | 281 ± 45 | 327 ± 21 | 19,000 ± 1,032 | 0 | 0 | 0 |
| Normal | N1 | 246 ± 41 | 4,902 ± 86 | 588 ± 59 | 10,129 ± 205 | 411 ± 32 | 215 ± 34 | 163 ± 26 |
| | N2 | 302 ± 26 | 6,592 ± 258 | 3,914 ± 406 | ND | 548 ± 42 | 442 ± 71 | 72 ± 8 |
| | N3 | 131 ± 27 | 2,068 ± 544 | 380 ± 51 | 2,677 ± 245 | 474 ± 14 | 296 ± 58 | 188 ± 34 |
| | N4 | 243 ± 49 | 6,573 ± 222 | 2,225 ± 99 | ND | 770 ± 25 | 572 ± 25 | 298 ± 20 |

*Peripheral blood mononuclear cells were assayed for mitogenic responses (shown as cpm of [$^3$H]thymidine incorporated) and for Ig-secreting cells (IgSC) of three isotypes induced by PWM plus CowanI(±SD). Typical results from each patient(tested at least twice) and parallel results from normal donors (N1-N4) are shown. IgM-secreting cells of normals and several group I patients at day 0 was less than 10 per 10$^4$ initial cells. ND, not done.

Differentiation to Ig secretion in Table 2 above was assayed under the most favorable conditions with a combination of T- and B-cell mitogens. To determine if B-cell defects in CVI patients of group I might be limited to distinct mitogen-responding subsets, peripheral blood mononuclear cells were cultured with each stimulant separately. For three group I patients studied, these cells responded to PWM and Cowan I alone but with reduced number of IgM-secreting cells compared to dual stimulation, (see Table 3 below), as seen with normal donors (Saiki, 0. et al. (1981) Supra). IgG and IgA secretion remained low or undetectable in all cases. Thus, patients in group I were qualitatively similar to each other by these assays, and no evidence for further defects in subsets of B cells required for IgM production was seen.

TABLE 3

Example of the pattern of Ig-secreting cell defects of group I patients; similar in different mitogenic conditions*

| Patient # | Stimulant | IgSC per 10⁴ initial cells | | |
|---|---|---|---|---|
| | | IgM | IgG | IgA |
| 1(3)+ | None | 0 | 0 | 0 |
| | PWM | 276 ± 17 | 7 ± 3 | 5 ± 1 |
| | Cowan I | 348 ± 23 | 15 ± 4 | 6 ± 2 |
| | PWM + Cowan I | 848 ± 23 | 11 ± 2 | 19 ± 4 |
| 3(3)+ | None | 0 | 0 | 0 |
| | PWM | 12 ± 2 | 0 | 2 ± 1 |
| | Cowan I | 32 ± 5 | 2 ± 1 | 0 |
| | PWM + Cowan I | 127 ± 6 | 8 ± 3 | 4 ± 1 |
| 4(1)+ | None | 0 | 0 | 0 |
| | PWM | 163 ± 38 | 3 ± 1 | 0 |
| | Cowan I | 273 ± 13 | 0 | 0 |
| | PWM + Cowan I | 408 ± 23 | 0 | 0 |
| N | None | 0-5 | 0-4 | 0-2 |
| | PWM | 43-247 | 41-153 | 24-164 |
| | Cowan I | 27-368 | 33-184 | 8-72 |
| | PWM + Cowan I | 355-904 | 151-849 | 102-276 |

*Patient peripheral blood mononuclear cells were assayed for induction of Ig-secreting cells (IgSC) with mitogen as shown. The range of values of normal donors (N) is given.
+Number of times assayed; typical results are shown.

Illustrations of Helper T cell and Supprepssor Effects in Patients

To determine if the B-cell malfunctions were primary B-cell defects or a result of suppression by other cells in the patents, first, T cells were partially depleted by one cycle of removing erythrocyte rossette-forming cells. Table 4 below shows that cells from T-cell-depleted normal donors retain mitogenic response to Cowan I and anti-mu, but the PWM response is greatly reduced. One or two patients from each group were also tested. Cells of patients from the first two groups, whose mononuclear cells showed proliferative responses to the B-cell mitogens, also responded when T cells were depleted. Removal of T cells from the peripheral blood mononuclear cells of patient 11 in group III did not restore proliferative responses to the B-cell mitogens, despite the presence of 30.8% surface IgM-positive (sIgM+) cells in the non-T-cell population.

TABLE 4

Example of effect of partial removal of T cells on mitogenicity*

| Patient # | Group | sIgM+ cells, % | Mitogenic response, cpm | | | |
|---|---|---|---|---|---|---|
| | | | 0 | Cowan I | Anti-mu | PWM |
| 1 | I | 24.2 | 160 ± 18 | 3,647 ± 92 | 903 ± 174 | 1,170 ± 398 |
| 4 | | 35.3 | 110 ± 23 | 2,072 ± 88 | 1,141 ± 186 | 230 ± 15 |
| 6 | II | 34.2 | 125 ± | 1,650 ± | 1,924 ± | 363 ± |

TABLE 4-continued

Example of effect of partial removal of T cells on mitogenicity*

| Patient # | Group | sIgM+ cells, % | Mitogenic response, cpm | | | |
|---|---|---|---|---|---|---|
| | | | 0 | Cowan I | Anti-mu | PWM |
| 7 | | 29.8 | 16 252 ± 16 | 145 2,761 ± 268 | 87 1,645 ± 179 | 24 1,341 ± 147 |
| 11 | III | 30.6 | 107 ± 12 | 106 ± 15 | 126 ± 18 | 340 ± 76 |
| N | | 38.4 | 251 ± 51 | 2,116 ± 223 | 806 ± 207 | 1,984 ± 155 |

*T cells were partially depleted form peripheral blood mononuclear cells by one cycle of erythrocyte-rosette formation, and the remaining cells were tested for mitogenic responses. Residual erythrocyte-rosetting cells amounted to 1-5% of the population. sIgM+ cells were determined by using fluorescent anti-IgM.

To study the role of patient T cells in their B-cell tefects, T and B cells were separated and assayed with normal cells for induction of Ig-secreting cells. Experiment A in Table 5, below shows that B cells from group I patients could produce IgM- but not IgG- or IgA-secreting cells when cultured with autologous or with normal donor T cells. In contrast, B cells from group II and III patients could not develop significant numbers of Ig-secreting cells with their own or with normal T cells. When T-cell-replacing factor was used with Cowan I inducer, B cells from group I patients produced only IgM-secreting cells (Table 5, experiment B), reflecting the pattern of their peripheral blood mononuclear cells (see Table 2), and the other patients showed no differentiation to Ig-secreting cells. This T-cell replacing factor induced IgM, IgG, and IgA in normal B cells (Table 5, experiment B). To study directly the activity of helper and suppressor T cells in patients, purified patient T cells were added to normal B cells or to normal B cells plus normal T cells, respectively. T cells from four patients tested allowed IgM, IgG, or IgA responses in normal donor B cells at 27-100% of Ig-secreting cell numbers obtained in control T-plus B-cell cultures (Table 6). The addition of patient T cells to cultures of normal B plus T cells also allowed Ig-secreting-cell responses at 51-109% of control values. Thus, defects in B cells from at least nine of the patients could not be restored by removal of T cells or by reconstitution with normal T cells or T-cell-replacing factor. Furthermore, T cells from at least four patients, covering groups I, II, and III can function in helping differentiation of normal B cells to IgM, IgG, and IgA secretion.

TABLE 5

Example of how patient B cells cannot differentiate to Ig-secreting cells with the help of normal T cells or purified T-cell factor

| Exp. | B-cell donor Patient # | Group | T-cell donor Patient # | IgSC per 10⁴ initial B-cell population | | |
|---|---|---|---|---|---|---|
| | | | | IgM | IgG | IgA |
| A* | 2 | I | 2 | 318 ± 20 | 0 | 0 |
| | | | N | 396 ± 17 | 4 ± 2 | 2 ± 1 |
| | 6 | II | 6 | 3 ± 1 | ND | ND |
| | | | N | 4 ± 1 | ND | ND |
| | 15 | III | 12 | 4 ± 2 | ND | ND |
| | | | N | 0 | ND | ND |
| | N | | N | 520 ± 32 | 472 ± 37 | 221 ± 31 |
| B+ | 1 | I | T-cell factor | 246 ± 20 | 3 ± 1 | 2 ± 1 |
| | 4 | | | 130 ± 24 | 0 | 0 |
| | 5 | II | | 0 | 0 | 0 |
| | 7 | | | 0 | 0 | 0 |
| | 11 | III | | 0 | ND | ND |
| | 13 | | | 0 | ND | ND |

TABLE 5-continued

Example of how patient B cells cannot differentiate to Ig-secreting cells with the help of normal T cells or purified T-cell factor

| Exp. | B-cell donor Patient # | Group | T-cell donor Patient # | IgSC per $10^4$ initial B-cell population | | |
|---|---|---|---|---|---|---|
| | | | | IgM | IgG | IgA |
| | 15 | | | 0 | 0 | 0 |
| | N | | | 133 ± 17 | 84 ± 11 | 82 ± 7 |

ND, not done.
*B cells were prepared by two cycles of erythrocyte-rosette depletion and contained less than 1% T cells; $10^5$ B cells plus $10^5$ T cells were assayed for Ig-secreting cells (IgSC) as in Table 2. B and T populations assayed separately had less than four IgSC per $10^4$ initial cells.
+B cells were assayed for induction of IgSC in the presence of Cowan I mitogen and 10% T-cell factor.

TABLE 6

Example of how patient T cells help normal B-cell differentiation to IgM-, IgG-, and IgA-secreting cells and do not inhibit normal T-cell helper activity*

| B-cell donor | T-cell donor | IgSC per $10^4$ initial B-cell population | | |
|---|---|---|---|---|
| | | IgM | IgG | IgA |
| N | N | 282 ± 37 | 156 ± 7 | 133 ± 5 |
| | 2 | 302 ± 14 | 135 ± 10 | 104 ± 15 |
| | 6 | 102 ± 15 | ND | ND |
| | 11 | 283 ± 43 | ND | ND |
| | 15 | 195 ± 13 | 94 ± 13 | 94 ± 11 |
| | — | 2 ± 1 | 0 | 2 ± 1 |
| N | N + N | 249 ± 40 | ND | ND |
| | N + 2 | 143 ± 58 | ND | ND |
| | N + 6 | 216 ± 18 | ND | ND |
| | N + 15 | 308 ± 26 | ND | ND |

ND, not done.
*Normal (N) donor B cells ($10^5$) were incubated alone (-) with $10^5$ T cells from various donors (Patients #2, 6, 11, 15), or with $10^5$ autologous T cells plus $10^5$ autologous or patient T cells. B cells and T cells assayed separately made less than 10 Ig-secreting cells (IgSC) in each Ig class.

The possibility of monocyte suppressors was also investigated. Monocytes were partially depleted by adherence to less than 1% of the cell population, and the remaining cells were tested for B-cell functions (Table 7). Nonadherent mononuclear cells from normal donors showed strong proliferation induced by Cowan I and anti-mu. Mitogen-induced Ig-secreting cells were observed also, but their numbers were reduced to 20–40% of that in cultures of total mononuclear cells, indicating the removal of monocyte helper influences. Nonadherent mononuclear cells from patients of the first two groups maintained positive mitogen responses to Cowan I and anti-mu, whereas two patients from the third group remained anergic in this assay. Only IgM-secreting cells were induced in nonadherent cells of donor 3, and no Ig-secreting cells were detected in nonadherent cell cultures of patients in groups II and III. Thus, the various B-cell defects observed in total peripheral blood mononuclear cell cultures from patients of all groups were not alleviated by removal of monocytes.

TABLE 7

Example of effects of partial removal of monocytes on mitogenicity and differentiation*

| Donor # | Mitogenic response, cpm | | | IgSC per $10^4$ initial cells | | |
|---|---|---|---|---|---|---|
| | 0 | Cowan I | Anti-mu | IgM | IgG | IgA |
| 3 | 315 ± 34 | 2,346 ± 213 | 2,783 ± 300 | 68 ± 7 | 2 ± 1 | 0 |
| 6 | 172 ± 22 | 602 ± 24 | 316 ± 42 | 4 ± 2 | 0 | 2 ± 1 |
| 7 | 199 ± 18 | 1,810 ± 172 | 2,364 ± 140 | 0 | 0 | 0 |
| 11 | 215 ± 33 | 263 ± 73 | 244 ± 41 | 0 | 0 | 0 |
| 15 | 402 ± 16 | 412 ± 23 | 401 ± 18 | 0 | 0 | 0 |
| N | 151 ± 10 | 2,618 ± 196 | 1,402 ± 155 | 118 ± 21 | 74 ± 9 | 44 ± 5 |

*Peripheral blood mononuclear cells were depleted of adherent cells and assayed; less than 2% of cells were phagocytic or esterasestaining. IgSC, Ig-secreting cells.

Immunodeficiency patients studied have a variety of B-cell defects not readily explained by malfunction of T cells or monocytes. The different types of defects were discovered by the use of several assays using B-cell mitogens in addition to the classical assay of T-cell-dependent PWM stimulation of B cells. Excess suppressor T cells (de la Concha E.G., et al. Supra, Siegal, F.P., et al. (1978) Supra; Cunningham-Rundles (1981) Supra) and suppressor monocytes (Siegal, F.P., et al. (1978) Supra) have been described in CVI, and defects in helper T cells and in adherent helper cells are to be expected. We did not find clear evidence for these types of defective B-cell regulation in our patient sample using in vitro assays for removal of T cells or monocytes or coculture of patient T cells with normal cells. However, long-term in vivo effects of other cell types in suppressing B-cell function cannot be excluded.

We have classified the patients studied into four clearly distinct groups based on elements of B cell assays (Table 8 below). However, it is obvious to those skilled in the art that further groups may be found by the methods of the present invention. Group I has normal mitogenic responses to Cowan I and anti-mu antibodies and can produce low-to-normal numbers of IgM-secreting cells in mitogen stimulation cultures. However, no differentiation of B cells to IgG or IgA secretion was observed. Group II patients have normal B-mitogen responses but no development of Ig-secreting cells of any class. Group III contains patients with nearly normal numbers of peripheral blood B cells but with no reaction in any of the B-cell functional assays, neither in mononuclear cell cultures (Table 2) nor in cultures of T-cell depleted B cells (Table 4). Group IV patients have virtually no sIg+ B cells and accordingly no functional responses. The defect in each group appears to be at a different stage of development, suggestive of normal B-cell maturation.

B cells of group I patients have the properties of mature, normal cells except they produce no Ig classes other than IgM. These cells may be blocked at a stage corresponding to immature cord blood B cells which, in some studies, produce mainly IgM (Ruuskanen, O., et al. (1980) J. Immunol. 126, 517–521; Nagaoki, T., et al. (1981) J. Immunol. 126, 2015–2019). CVI patients of group I may have a defect at the DNA level in genetic switching mechanisms for expression of non-IgM isotypes (Kataoka, T., et al. (1980) Proc. Nat'l. Acad. Sci. USA 77, 919–922).

B cells of group II are blocked in differentiation to Ig-secreting cells but express proliferative responses. They may lack receptors for T-cell signals inducing differentiation, or they may bind T-cell factor but not transmit this information intracellularly.

Group III B cells have SIg expressions but lack the functional B-cell properties tested. These patient B cells bind anit-mu antibodies (and presumably Cowan I mitogen) but fail to proliferate. These B cells may be blocked in development of membrane or intracellular mechanisms for transmitting mitogenic signals to the nucleus.

TABLE 8

Example of classification of immunodeficient patients with primary B-cell defects into subsets with possible correlation to stages of B-cell development

| Type | Response to mitogen | | Differentiation to IgSC | | | Stage of B-cell differentiation |
| --- | --- | --- | --- | --- | --- | --- |
| | Cowan I | Anti-mu | IgM | IgG | IgA | |
| Normal | + | + | + | + | + | Normal mature |
| I | + | + | + | − | − | IgM differentiation only |
| II | + | + | − | − | − | Proliferation only |
| III | − | − | − | − | − | Unresponsive B cells |
| IV | − | − | − | − | − | No Ig-positive cells |

IgSC, Ig-secreting cells.

Schuurman et al. (Schuurman, K.R.B., et al. (1980) J. Immunol. 125, 820–824) found that five of five CVI patients with sIg+ cells responded mitogenically to Cowan I. In our study, 10 of 12 patients with appreciable numbers of B cells showed proliferation in response to Cowan I and anti-mu, but two (nos. 11 and 12) were nonresponders.

Other methods for studying immunodeficient patients may allow further distinctions in the pathogenicity of these diseases, such as the use of T-cell-independent Epstein-Barr virus (Mitsuya, H., et al. (1981) J. Immunol. 127, 311–315). Pahwa et al. (Pahwa, S.G., et al. (1982) J. Clin. Immunol., in press) defined several categories of CVI with respect to in vitro induction of IgM antibody responses to sheep erythrocytes: (i) normal; (ii) low or absent but stimulated by extra T-cell help provided by concanavalin A or allogeneic, irradiated T cells; and (iii) completely unresponsive. The classification scheme as shown in Table 8 based on the methods above will aid in diagnosis and ultimately in therapy for this group of diseases. These methods can also be used in conjunction with other CVI testing methods as well to confirm as well as improve diagnosis and therapy.

What is claimed:

1. Method for differential diagnosis of subclasses in common varied immunodeficiency disease group which comprises
   (a) contacting human peripheral blood B-cell specimens with stimulatory mitogen factor cowan I or the F(ab')2 fragment of anti-Ig mu antibody chain;
   (b) assaying for Sig expression, cell proliferation and differentiation to immunoglobulin screting cells; and
   (c) identifying the elements of SIg expression, cell proliferation and differentiation with a B-cell common varied immunodeficiency subclass wherein;
   subclass I contains B cells which exhibit the elements of SIg expression, cell proliferation and differentiation to immunoglobulin secreting cells producing essentially only IgM,
   subclass II contains B cells which exhibit only the element of cell proliferation, without SIg expression and without differentiation to immunoglobulin secreting cells,
   subclass III contains B cells which exhibit only the elemnt of SIg expression with failure to prolierate and no differentiation to immunoglobulin secreting cells, and
   subclass IV contains B cells which fail to exhibit the elements of SIg expression, proliferation and differentiation to immunoglobulin secreting cells.

2. Method of claim 1, wherein the assay comprises incorporation of a labelled nucleic acid derivative by B cell specimens.

3. Method of claim 1 wherein the assay for B-cell stimulation comprises a determination for the element of B-cell proliferation.

4. Method of claim 1, wherein the assay comprises the binding of an F(ab')2 fragment of an anti-Ig mu chain antibody to a B-cell specimen.

* * * * *